(12) United States Patent
Kopca

(10) Patent No.: US 8,317,271 B1
(45) Date of Patent: Nov. 27, 2012

(54) CHAIR OCCUPANT SUPPORT VEST

(75) Inventor: Alexis Basabe Kopca, West Allis, WI (US)

(73) Assignee: Adaptive Engineering Lab, Inc., Germantown, WI (US)

(*) Notice: Subject to any disclaimer, the term of this patent is extended or adjusted under 35 U.S.C. 154(b) by 67 days.

(21) Appl. No.: 13/106,512

(22) Filed: May 12, 2011

(51) Int. Cl.
 *A62B 35/00* (2006.01)
(52) U.S. Cl. ........................................ 297/465
(58) Field of Classification Search .............. 297/465, 297/464; 128/875; 2/102
See application file for complete search history.

(56) References Cited

U.S. PATENT DOCUMENTS

| 4,330,152 A | 5/1982 | Legan et al. |
| 4,891,846 A | 1/1990 | Sager et al. |
| 5,008,959 A | 4/1991 | Coppage, Jr. et al. |
| 5,327,811 A | 7/1994 | Price et al. |
| 5,562,326 A * | 10/1996 | Stroud ............................ 297/465 |
| 5,730,498 A * | 3/1998 | Hanson et al. ................. 297/465 |
| D403,125 S | 12/1998 | Larsen et al. |
| 6,076,527 A | 6/2000 | Rottinghaus et al. |
| 7,628,157 B2 | 12/2009 | Kosh |
| D627,072 S | 11/2010 | Kosh |

\* cited by examiner

*Primary Examiner* — Milton Nelson, Jr.
(74) *Attorney, Agent, or Firm* — Quarles & Brady LLP; George E. Haas

(57) ABSTRACT

A support vest, for limiting movement of a person in a chair, has a body that includes a central section adapted to fit against an anterior portion of the trunk of the person. A pair of shoulder straps project upward from the central section to fit against the person's shoulders. The body is formed by a resilient perforated core pad and layers a mesh fabric that abut the major surfaces of the core pad. A outer cover abuts one of the second layer of a mesh fabric layers and is formed by a resilient perforated nucleus pad encased is a breathable fabric. This layered body is breathable and has materials that wick perspiration away from the person.

19 Claims, 2 Drawing Sheets

CHAIR OCCUPANT SUPPORT VEST

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to articles for supporting a person seated in a chair, and more particularly to such articles that support and limit the person from leaning too far forward.

2. Description of the Related Art

Many individuals, who require the use of a wheelchair, are sufficiently frail or infirmed so as to be incapable of supporting themselves within the wheelchair seat. For example, a patient seated in the wheelchair frequently slouches, slumps, slides down, and leans to one side or forward at the waist. Thus, these individuals require some form of posture support that maintains the person in a upright seated position.

Such posture support, while being sufficiently supportive, must be comfortable and able to stretch somewhat to allow the person to move enough to perform normal functions, such as eating and working at a desk.

SUMMARY OF THE INVENTION

A support vest, for limiting movement of a person in a chair, has a body adapted to fit against an anterior portion of the trunk of the person. The body includes a central section with opposing first and second edges. A pair of shoulder straps of the body project from the first edge of the central section and are spaced apart so as to be adapted to fit onto both shoulders of the person. A pair of tabs project from the second edge of the central section and are spaced apart, such as for example, so that each tab can fit against opposite sides of the person.

The body is formed as a multiple layer structure comprising a core layer of a resilient material that has perforations extending between first and second major surfaces. A first layer of a mesh fabric abuts the first major surface. A cover extends over the second major surface of the core layer. The cover has a nucleus layer of a resilient material that has perforations extending there through and has a first jacket layer of a breathable fabric abutting the nucleus layer on an opposite side from the core layer.

Another aspect of the support vest is that the mesh fabric has greater stretchability in a first direction extending between the first and second edges than stretchability in a second direction orthogonal to the first direction.

In one particular embodiment, the support vest also has a second layer of a mesh fabric abutting the second major surface of the core layer, and a second jacket layer of a breathable fabric between the nucleus layer and the core layer.

DETAILED DESCRIPTION OF THE INVENTION

Figure 1:
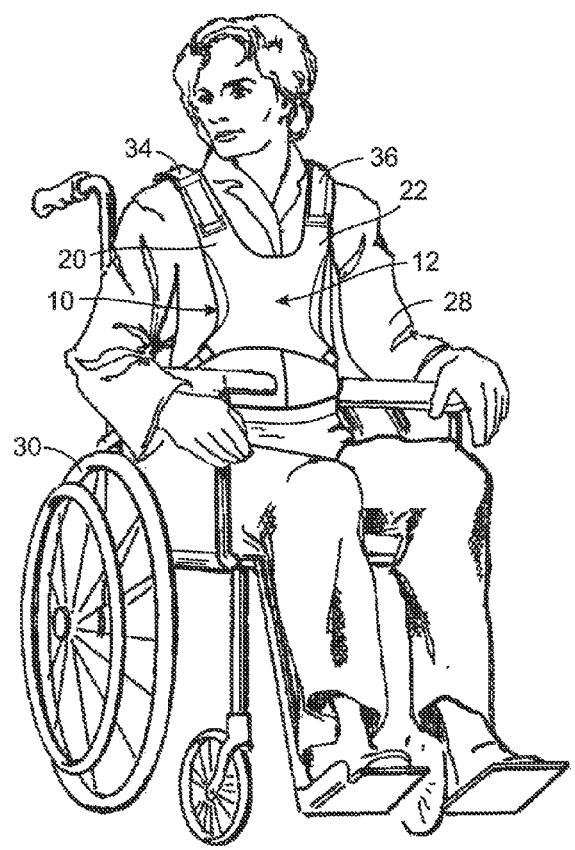
FIG. 1 depicts a person retained in a wheelchair by a support vest according to the present invention.

References herein to directional relationships and movement, such as upper and lower or left and right, refer to the relationship and movement of the components in the orientation illustrated in the drawings, which may not be the orientation of the components when in use.

Figure 2:
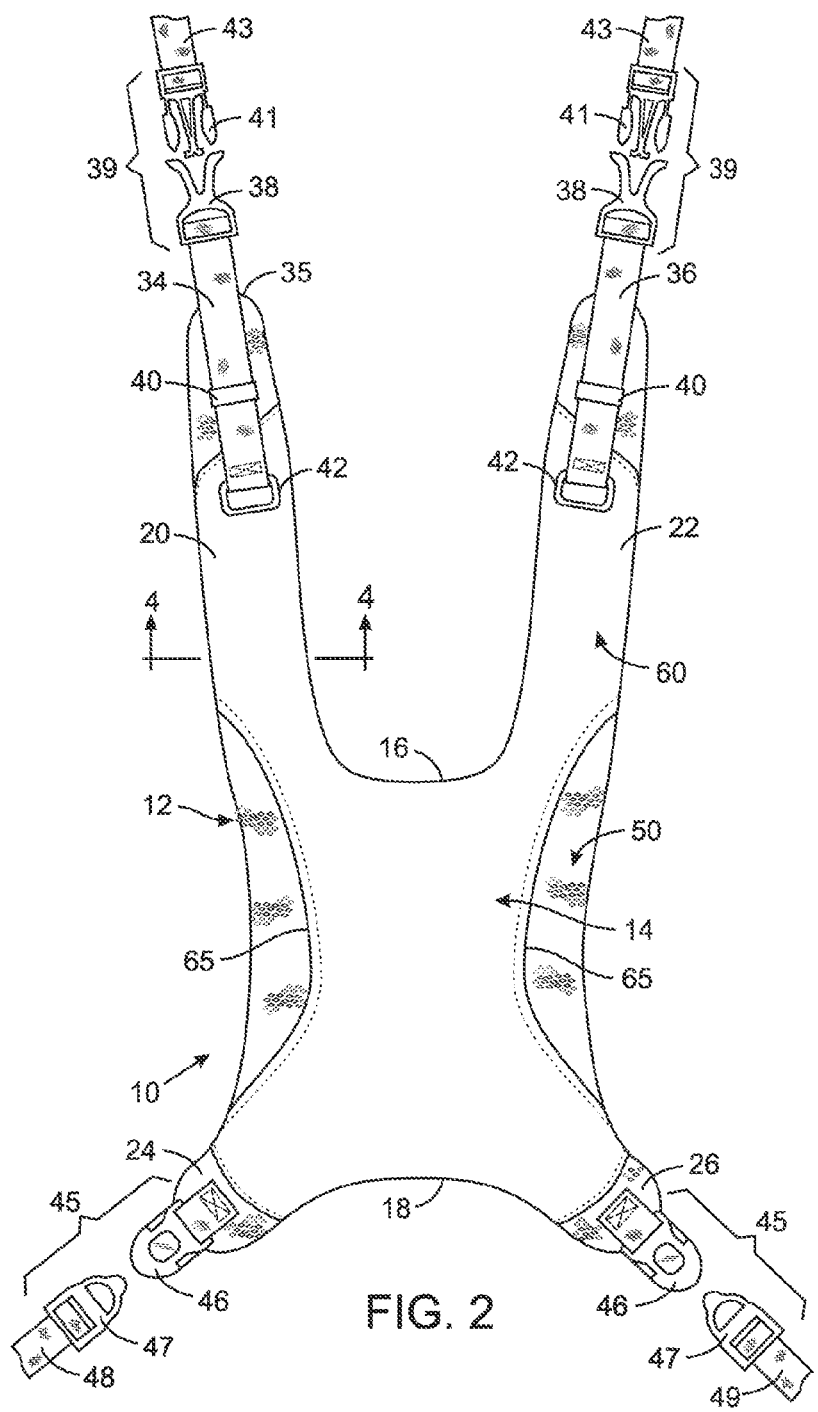
FIG. 2 is a front view of the support vest.

With reference to FIGS. 1 and 2, a support vest 10 is adapted to fit against the anterior portion of the trunk of a person 28 sitting in a wheelchair 30 and is particularly adapted to fit against the chest of the person. Alternatively the support vest 10 can be place lower on the person's trunk, such as against the lower ribs or upper abdomen. The support vest 10 includes a body 12 which has a central portion 14 with opposing first and second edges 16 and 18, respectively. A pair of shoulder straps 20 and 22 project upward from the first edge 16 of the central portion 14. The two shoulder straps 20 and 22 are spaced apart along the first edge 16 of the vest body 12 so as to extend upward onto both shoulders of the person.

Figure 3:
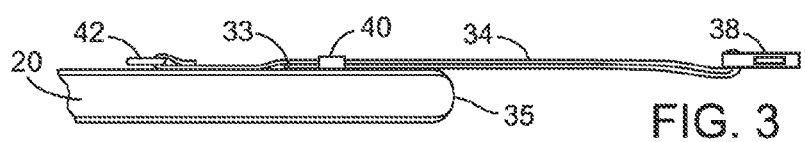
FIG. 3 is an partial cutaway side view of the support vest showing a fastening strap that attaches to the wheelchair.

First and second fastening straps 34 and 36 are connected to the first and second shoulder straps 20 and 22, respectively. The details of the first fastening strap 34 will be described with the understanding that the second fastening strap 36 is of identical construction, except it is attached to the other shoulder strap 22. With reference to FIG. 3, one end 33 of the first fastening strap 36 is attached, such as by sewing, to the first shoulder strap 20 slightly spaced from the upper end 35. The first fastening strap 34 projects upward from the upper end 35 and winds through the socket portion 38 of a releasable shoulder fastener 39. The winding path through the socket portion 38 prevents the first fastening strap 34 from sliding through the socket portion when the strap and releasable shoulder fastener 39 secure the support vest around the person. From that shoulder fastener 39, the first fastening strap 34 returns back over itself and the outer surface of the first shoulder strap 20. That returning portion of the first fastening strap 36 passes under a belt loop 40 that is attached, such as by sewing, to the outer surface of the first shoulder strap 20. The other end of the first fastening strap 34 then loops through a pull ring 42 which facilitates an individual grasping that end of the fastening strap for adjustment purposes. In order to adjust the position of the shoulder fastener 39, the tension of the first fastening strap 34 must be relieved and engagement of the strap with the socket portion 38 slackened. In that slackened state, a person can pull on the ring 42 and slide the fastening strap through the fastener socket portion 38 to the desired position.

The shoulder fastener 39 also has a plug portion 41 that is configured to be inserted into and releasably engage the socket portion 38. The plug portion 41 is mounted to an end of a back strap 43 that is attached to the seat back or upper frame of the wheelchair 30 so as to secure the fastening strap 34 to the wheelchair.

Referring still to FIGS. 1 and 2, a pair of tabs 24 and 26 project downward from the second edge 18 of the central portion 14 of the vest body 12. The tabs 24 and 26 are spaced apart along the second edge 18 so as to be located at opposite lower corners of the body 12. The two tabs 24 and 26 extend partially against opposite sides of the person 28 seated in the wheelchair 30. Each tab 24 and 26 is attached to a separate side strap 48 and 49, respectively, by a releasable side fastener 45. Each side fastener 45 comprises a socket portion 46 and a plug portion 47 adapted to releasably engage the socket portion. The plug portion 47 is attached to the respective side strap 48 or 49, which as shown in FIG. 1 extends around one side of the person 28 seated in the wheelchair 30 and is secured to either the frame of the wheelchair. Alternatively, each side strap 48 or 49 can be secured to seat of the wheelchair so that the support vest 10 is placed lower on the person with the second edge 18 of the vest body 12 laying against the person's lower ribs or abdomen. In this latter position. the tabs 24 and 26 extend against opposite sides of the person's trunk.

The sets of fasteners 39 and 45 being releasable allow the support vest 10 to be easily fastened around the person seated in the wheelchair so as to limit the motion of that person while seated. Those fasteners 39 and 45 also allow the support vest 10 to be easily removed from around the person.

It should be appreciated that the connections of the socket and plug portions of the shoulder fasteners 39 and the side fasteners 45 to the different straps can be reversed. In addition, other types of releasable strap fastening devices can be used for the shoulder and side fasteners.

Figure 4:
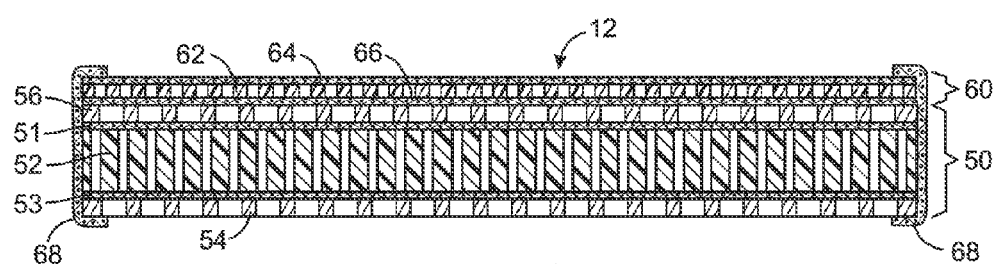
FIG. 4 is a cross-section through the support vest along line 4-4 in FIG. 2.

The body 12 of the support vest 10 has a unique multiple layer construction which enhances the comfortableness of the vest. With additional reference to the cross section through the vest body 12 shown in FIG. 4, a foundation 50 extends throughout the entire vest body and specifically from the remote ends of the shoulder straps 20 and 22 through the central portion 14 to the tips of the tabs 24 and 26. The foundation 50 comprises a core layer formed by a core pad 52 of a resilient material with perforations extending between its first and second major surfaces. For example, the resilient material may be a synthetic rubber, such as a polymerization of chloroprene, one type of which is commonly referred to as neoprene. In one embodiment, the core pad 52 is at least 5.0 mm thick (e.g. 6.0 mm) with approximately 1.0 mm diameter perforations spaced in a two dimensional array on approximately 4.0 mm centers to provide sufficient air flow through the core pad to properly ventilate the support vest. A first covering layer 51 is bonded, such as by an adhesive, to one exterior major surface of the core pad 52 and a second covering layer 53 is similarly bonded to the other exterior major surface of the core pad. The first and second covering layers 51 and 53 are formed of a breathable material, such as a microfiber polyester fabric, which allows air to pass there through. The term "breathable" as used herein means that the related material is sufficiently porous to allow air the pass there through.

The first and second covering layers 51 and 53 over the core pad 52 are respectively covered by first and second layers 54 and 56 of a mesh fabric, one type of which is commonly referred to as an air mesh fabric. For example, each mesh fabric layer 54 and 56 may be 3 mm thick with openings over approximately one-quarter of the surface area. The first layer of 54 of the mesh fabric is proximate to the person 28 wearing the support vest 10.

Most of the outer surface of the foundation 50, i.e., the surface that is remote from the person, is protected by a cover 60 that abuts the second layer of 56 of the mesh fabric. The cover is easier to clean than the outer mesh fabric layers 54 and 56 of the foundation. As shown in FIG. 2, the cover 60 extends from near the tips of the shoulder straps 20 and 22 across the center section 14 of the support vest 10 to locations near the tips of the tabs 24 and 26. In some versions of the support vest 10, such as the one illustrated, the mid-section of the cover 60 curves inward at section 65 from the lateral edges of the foundation 50.

Referring again to FIG. 4, the cover 60 comprises a nucleus layer formed by a nucleus pad 62 which may comprise the same resilient material as used for the foundation core pad 52. The nucleus pad 62 may be less that 1.5 mm (e.g. 1.0 mm) thick with approximately 1.0 mm diameter perforations in a two dimensional array. The exterior surface of the nucleus pad 62 is covered by a first jacket layer 64, and a second jacket layer 66 is provided between the nucleus pad 62 and the foundation 50. The first and second jacket layers 64 and 66 are formed of a breathable material, such as a microfiber polyester fabric, which allows air to pass there through.

The breathable nature of the fabrics and perforations through the other layers allows air to pass through the support vest 10. This breathability enables the body heat of the person to escape and enabled perspiration to evaporate. Furthermore the various layers are formed of materials that wick perspiration away from the vest wearer.

The edge of the body 12 is wrapped in a band 68, such as a bias tape, that is stitched through the body to not only secure the band to the body but also hold the layers together. Additional stitching at the edges of the cover that extend inward from the edges of the foundation also are stitched through the foundation to further secure the layers of material together.

All the layers of the body are stretchable with at least the mesh fabric layers 54 and 56 having a greater stretchability in a first direction extending between the first and second edges 16 and 18 of the central section, i.e. in the vertical direction, than the stretchability in a second direction that is orthogonal to the first direction, i.e. generally horizontal when the support vest is worn.

As an optional feature, a zipper can extend vertically between the first and second edges 16 and 18 of the central portion 14 of the body 12. This zipper facilitates placing and removing the support vest 10 around the seated person 28 without having the unfasten any of the straps 34, 36, 48 or 49. In fact, providing a zipper could eliminate the need for releasable fasteners on those straps, which while still being adjustable would be non-releasably fastened to the support vest body 12 and the wheelchair 30.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. A support vest, for controlling movement of a person in a chair, comprising:
   a body that includes a central section adapted to fit against an anterior portion of the trunk of the person and having opposing first and second edges, a pair of shoulder straps projecting from the first edge of the central section and spaced apart so as to be adapted to fit against both shoulders of the person, and a pair of tabs projecting from the second edge of the central section and spaced apart;
   wherein the body comprises a core layer of a resilient material that has perforations extending between first and second major surfaces, a first layer of a mesh fabric abutting the first major surface, and a cover extending over the second major surface of the core layer, wherein the cover has a nucleus layer of a resilient material that has perforations extending there through and has a first jacket layer of a breathable fabric abutting the nucleus layer on an opposite side from the core layer.

2. The support vest as recited in claim 1 wherein the mesh fabric has greater stretchability in a first direction extending between the first and second edges than stretchability in a second direction orthogonal to the first direction.

3. The support vest as recited in claim 1 further comprising a pair of side straps, each connected to one of the tabs for attaching the support vest to the chair.

4. The support vest as recited in claim 1 further comprising a second jacket layer of a breathable fabric between the nucleus layer and the core layer.

5. The support vest as recited in claim 1 further comprising first and second fastening straps respectively connected to the first and second shoulder straps for attaching the support vest to the chair.

6. The support vest as recited in claim 1 wherein the resilient material of at least one of the core layer and the nucleus layer is a polymerization of chloroprene.

7. The support vest as recited in claim 1 wherein the resilient material of at least one of the core layer and the nucleus layer comprises a synthetic rubber.

8. The support vest as recited in claim 1 further comprising a second layer of a mesh fabric abutting the second major surface of the core layer.

9. The support vest as recited in claim 8 wherein the first and second jacket layers comprise a polyester fabric.

10. The support vest as recited in claim 8 wherein the first and second jacket layers comprise a microfiber fabric.

11. A support vest, for limiting movement of a person in a chair, comprising:
   a body that includes a central section adapted to fit against an anterior portion of the trunk of the person and having opposing first and second edges, a pair of shoulder straps projecting from the first edge of the central section and spaced apart so as to be adapted to fit on both shoulders of the person, and a pair of tabs projecting from the second edge of the central section and spaced apart;
   wherein the body comprises a core pad of a resilient material that has perforations extending between first and second major surfaces, a first layer of a mesh fabric abutting the first major surface, a second layer of a mesh fabric abutting the second major surface, and a cover abutting the second layer of a mesh fabric, wherein the cover has a nucleus layer of a resilient material that has perforations extending there through and a first jacket layer of a breathable fabric abutting the nucleus layer on an opposite side from the first layer of a mesh fabric.

12. The support vest as recited in claim 11 wherein the mesh fabric has stretchability in a first direction extending between the first and second edges that is greater than stretchability in a second direction orthogonal to the first direction.

13. The support vest as recited in claim 11 further comprising a second jacket layer of a breathable fabric between the nucleus layer and the core layer.

14. The support vest as recited in claim 13 wherein the first and second jacket layers comprise a polyester fabric.

15. The support vest as recited in claim 13 wherein the first and second jacket layers comprise a microfiber fabric.

16. The support vest as recited in claim 11 wherein the resilient material of at least one of the core layer and the nucleus layer is a synthetic rubber.

17. The support vest as recited in claim 11 wherein the resilient material of at least one of the core layer and the nucleus layer is a polymerization of chloroprene.

18. The support vest as recited in claim 11 further comprising first and second fastening straps respectively connected to the first and second shoulder straps for attaching the support vest to the chair.

19. The support vest as recited in claim 11 further comprising a pair of side straps each connected to one of the tabs for attaching the support vest to the chair.

\* \* \* \* \*